United States Patent
DiFoggio

(10) Patent No.: US 10,215,741 B2
(45) Date of Patent: Feb. 26, 2019

(54) DIFFUSION CHROMATOGRAPHY FLUID ANALYSIS

(71) Applicant: BAKER HUGHES INCORPORATED, Houston, TX (US)

(72) Inventor: Rocco DiFoggio, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 198 days.

(21) Appl. No.: 15/147,742

(22) Filed: May 5, 2016

(65) Prior Publication Data
US 2017/0322191 A1    Nov. 9, 2017

(51) Int. Cl.
*G01N 30/86* (2006.01)
*G01N 30/00* (2006.01)
(Continued)

(52) U.S. Cl.
CPC ......... *G01N 30/8675* (2013.01); *G01N 30/00* (2013.01); *G01N 33/2823* (2013.01);
(Continued)

(58) Field of Classification Search
CPC ............ G01N 13/00; G01N 2030/746; G01N 2030/8854; G01N 30/00; G01N 30/74; G01N 30/8675; G01N 33/2823
See application file for complete search history.

(56) References Cited

U.S. PATENT DOCUMENTS 5,770,088 A * 6/1998 Ikeda ................. B01D 15/1828
210/198.2

6,696,240 B1 * 2/2004 Kloepfer .............. G01N 33/558
422/412
(Continued)

FOREIGN PATENT DOCUMENTS

DE     4128846 A1 *  3/1993   ......... G01N 21/7703
EP     3211398 A1 *  8/2017   ............. G01N 13/00
(Continued)

OTHER PUBLICATIONS

Umezawa, S., and A. Nagashima. "Measurement of the diffusion coefficients of acetone, benzene, and alkane in supercritical CO2 by the Taylor dispersion method." The Journal of Supercritical Fluids 5.4 (1992): Abstract.*
(Continued)

*Primary Examiner* — Harshad R Patel
*Assistant Examiner* — Punam Roy
(74) *Attorney, Agent, or Firm* — Mossman, Kumar & Tyler, PC

(57) ABSTRACT

Methods, systems, devices, and products for evaluating a fluid. Methods include introducing a sample comprising the fluid to a solvating fluid at a point in a chamber associated with the instrument at a first time to create a heterogeneous admixture; measuring concentrations of each of a plurality of components in the admixture at a plurality of distances from the point in the chamber at, at least one additional time later than the first time, each of the plurality of distances being non-zero; and estimating a relative concentration for each of the plurality of components in the fluid by extrapolating the relative concentration of each of the plurality of components in the sample at the point at the first time using the measured concentrations in the admixture at the plurality of distances.

15 Claims, 10 Drawing Sheets

(51) Int. Cl.
*G01N 33/28* (2006.01)
*G01N 30/88* (2006.01)
*G01N 30/74* (2006.01)
*G01N 13/00* (2006.01)

(52) U.S. Cl.
CPC .............. *G01N 13/00* (2013.01); *G01N 30/74* (2013.01); *G01N 2030/746* (2013.01); *G01N 2030/8854* (2013.01)

(56) References Cited

U.S. PATENT DOCUMENTS

| | | | | |
|---|---|---|---|---|
| 6,858,436 | B2* | 2/2005 | Zenhausern | G01N 21/552 |
| | | | | 250/306 |
| 6,941,825 | B2* | 9/2005 | Pawliszyn | G01N 30/00 |
| | | | | 422/69 |
| 7,039,527 | B2* | 5/2006 | Tripathi | G01N 13/00 |
| | | | | 702/27 |
| 7,384,453 | B2* | 6/2008 | Bostrom | G01N 30/32 |
| | | | | 73/23.42 |
| 7,608,818 | B2* | 10/2009 | Miller | G01N 27/624 |
| | | | | 250/281 |
| 8,028,562 | B2* | 10/2011 | Shah | E21B 47/10 |
| | | | | 73/23.35 |
| 8,574,920 | B2* | 11/2013 | Caron | G01N 30/74 |
| | | | | 385/12 |
| 9,170,242 | B2* | 10/2015 | Derenzo | G01N 30/62 |
| 9,664,665 | B2* | 5/2017 | Gisolf | E21B 49/087 |
| 9,739,709 | B2* | 8/2017 | Lear | G02B 6/1221 |
| 9,841,418 | B2* | 12/2017 | Hanashi | G01N 21/6408 |
| 2009/0128812 | A1* | 5/2009 | Keller | G01N 15/1404 |
| | | | | 356/338 |
| 2009/0321356 | A1* | 12/2009 | Gerhardt | G01N 30/606 |
| | | | | 210/656 |
| 2011/0113866 | A1* | 5/2011 | Finlay | G01N 30/6095 |
| | | | | 73/61.52 |
| 2012/0138154 | A1* | 6/2012 | Grosso | B01L 3/5023 |
| | | | | 137/1 |
| 2013/0161243 | A1* | 6/2013 | Kanomata | G01N 30/74 |
| | | | | 210/85 |
| 2016/0116403 | A1* | 4/2016 | Lear | G02B 6/1221 |
| | | | | 356/70 |
| 2016/0238571 | A1* | 8/2016 | Welz | G01N 30/0005 |
| 2017/0184490 | A1* | 6/2017 | Marshall | G01N 21/1717 |

FOREIGN PATENT DOCUMENTS

| | | | |
|---|---|---|---|
| RU | 2569752 C2 * | 11/2015 | |
| WO | WO 03102520 A1 * | 12/2003 | G01J 3/26 |

OTHER PUBLICATIONS

Manz, Andréas, N. Graber, and H. áM Widmer. "Miniaturized total chemical analysis systems: a novel concept for chemical sensing." Sensors and actuators B: Chemical 1.1-6 (1990): 244-248.*

Elshahawi, H., et al. "Current State and Future Trends in the Use of Downhole Fluid Analysis for Improved Reservoir Evaluation." SPE Annual Technical Conference and Exhibition. Society of Petroleum Engineers, 2016.*

Guiochon, Georges, and Abhijit Tarafder. "Fundamental challenges and opportunities for preparative supercritical fluid chromatography." Journal of Chromatography A 1218.8 (2011): 1037-1114.*

Stahl, Egon, and W. Schilz. "Extraction with supercritical gases in coupling with thin-layer chromatographyExtraktion mit überkritischen Gasen in Kopplung mit der Dünnschicht-Chromatographie." Fresenius' Zeitschrift für analytische Chemie 280.2 (1976): 99-104.* del C Salvatierra-Stamp, Vilma, et al. "Supercritical-Fluid Chromatography with Diode-Array Detection for Emerging Contaminants Determination in Water Samples. Method Validation and Estimation of the Uncertainty." Journal of Chromatography & Separation Techniques 6.6 (2015): 1.*

Yonker, C. R., and R. D. Smith. "Solvatochromic behavior of binary supercritical fluids: the carbon dioxide/2-propanol system." The Journal of Physical Chemistry 92.8 (1988): 2374-2378.*

U. Liddel et al., "Spectral Differentiation of Pur Hydrocarbons: A Near Infrared Absorption Study," Research Paper RP610, Part of Bureau of Standards Jnl of Research, vol. 11, pp. 599-618 (Nov. 1933).

H. Feng et al., "Molecular Dynamics Simulation of Diffusion and Structure of Some n-Alkanes in near Critical and Supercritical Carbon Dioxide at Infinite Dilution," N. Phys. Chem 8, 117, pp. 12525-12534 (2013.

* cited by examiner

DIFFUSION CHROMATOGRAPHY FLUID ANALYSIS

FIELD OF THE DISCLOSURE

This disclosure generally relates to borehole tools, and in particular to methods and apparatuses for conducting downhole measurements.

BACKGROUND OF THE DISCLOSURE

Drilling wells for various purposes is well-known. Such wells may be drilled for geothermal purposes, to produce hydrocarbons (e.g., oil and gas), to produce water, and so on. Well depth may range from a few thousand feet to 25,000 feet or more. In hydrocarbon wells, downhole tools often incorporate various sensors, instruments and control devices in order to carry out any number of downhole operations. Thus, the tools may include sensors and/or electronics for formation evaluation, fluid analysis, monitoring and controlling the tool itself, and so on. Tools that allow testing of fluid properties using instruments located downhole are known. It is also well known to use laboratory techniques such as liquid chromatography and gas chromatography to analyze fluids in surface analysis.

SUMMARY OF THE DISCLOSURE

Aspects of the present disclosure include methods, systems, and devices for evaluating a fluid using an instrument. General method aspects include introducing a sample comprising the fluid to a solvating fluid at a point in a chamber associated with the instrument at a first time to create a heterogeneous admixture; measuring concentrations of each of a plurality of components in the admixture at a plurality of distances from the point in the chamber at, at least one additional time later than the first time, each of the plurality of distances being non-zero; and estimating a relative concentration for each of the plurality of components in the fluid by extrapolating the relative concentration of each of the plurality of components in the sample at the point at the first time using the measured concentrations in the admixture at the plurality of distances.

At least some of the measured concentrations of a particular component of the plurality of components at the plurality of distances may be non-identical due to diffusion of the plurality of components over time. Methods may include estimating a diffusion curve for each of the plurality of components from the measured concentrations; estimating a diffusion coefficient for each of the plurality of components from the diffusion curve; and estimating the relative concentration for each of the plurality of components using at least the diffusion coefficient. Diffusion curves may be expressed, processed, rendered, manipulated, or stored as a mathematical representation, such as an equation.

The solvating fluid may be supercritical carbon dioxide, and the sample is injected in the solvating fluid in the chamber at a pressure greater than an ambient pressure of the solvating fluid. Measuring the concentrations of each of the plurality of components at the plurality of distances may include providing illumination to the chamber; and using a plurality of optical sensors to detect, at each of the plurality of distances, absorption of wavelengths of the illumination that are characteristic of the plurality of components. The plurality of optical sensors may include at least one of: i) a photodiode array; and ii) a pyroelectric array. The illumination may comprise at least one of: i) visible light; ii) near-infrared light; and iii) mid-infrared light.

The absorption of the wavelengths may be measured using a plurality of wavelength bands such that each of the plurality of components is characterized by one or more wavelength bands, and wherein the relative concentration of each of the plurality of components in the admixture is estimated simultaneously. The absorption of the wavelengths may be measured over a wavelength band sufficiently broad to be responsive to all of the plurality of components, and the relative concentration of each of the plurality of components in the admixture is estimated in sequence.

The sequence may include a plurality of stages and wherein the first stage begins at a first additional time of the at least one additional time after introducing the sample, the first stage comprising: i) measuring concentrations of a lightest component of the plurality of components at the plurality of distances from the point; ii) estimating the diffusion curve for the lightest component from the concentrations of the lightest component; iii) estimating the diffusion coefficient for the lightest component from the corresponding diffusion curve for the lightest component; and iv) performing additional measurement cycles. The sequence may include additional stages iteratively performed on a lightest component untested in a preceding stage, each additional stage comprising: i) allowing the lightest component untested of the plurality of components to reach sufficient diffusion by waiting for another time interval; ii) measuring concentrations of the lightest component untested in combination with tested components at the plurality of distances; iii) estimating the diffusion curve for the lightest component untested from the measured concentrations of the lightest component untested in combination with tested components at the plurality of distances using the diffusion curve corresponding to each of the tested components; iv) estimating the diffusion coefficient for the lightest component untested from the diffusion curve for the lightest component untested.

Estimating the diffusion curve for the lightest component untested from the measured concentrations of the lightest component untested in combination with the tested components at the plurality of distances may include: estimating a cumulative diffusion curve for the lightest component untested in combination with tested components; and subtracting the diffusion curves corresponding to each of the tested components from the cumulative diffusion curve to estimate the diffusion curve for the lightest component untested.

The components may include hydrocarbons. Methods may include filtering the admixture to recover the solvating fluid; and reusing the solvating fluid on additional samples. Methods may include estimating a parameter of interest of the fluid using at least a portion of the estimated relative concentration for each of the plurality of components. The fluid may include a downhole fluid obtained using a borehole intersecting an earth formation. Methods may include conveying a sampling tool in the borehole, wherein the instrument is associated with the sampling tool; and drawing the downhole fluid into the tool.

General apparatus embodiments may include a chamber associated with the instrument fillable with solvating fluid; a source of solvating fluid coupled to the chamber; an injector configured to introduce the fluid to the chamber; an illumination source; an optical sensor array; and at least one processor configured to: fill the chamber with solvating fluid from the source of solvating fluid; introduce a sample comprising the fluid to the solvating fluid at a point in the chamber at a first time using the injector to create a heterogeneous admixture; measure concentrations of each of a plurality of components in the admixture at a plurality of distances from the point in the chamber at, at least one additional time later than the first time, each of the plurality of distances being non-zero, using the illumination source and the optical sensor array; estimate a relative concentration for each of the plurality of components in the fluid by extrapolating the relative concentration of each of the plurality of components in the sample at the point at the first time using the measured concentrations in the admixture at the plurality of distances.

Apparatus embodiments may include at least one processor and a non-transitory computer-readable medium product accessible to the processor comprising instructions for taking measurements and in some cases estimating at least one parameter of interest of the fluid. The apparatus may be configured for use as part of a downhole tool assembly, including a bottom hole assembly disposed on a drill string. The processor may include instructions for taking measurements and/or estimating at least one parameter of interest relating to an earth formation intersected by a borehole disposed on the medium that, when executed by a processor, cause the at least one processor to execute one or more methods or method components as described herein.

Examples of some features of the disclosure may be summarized rather broadly herein in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

Figure 1:
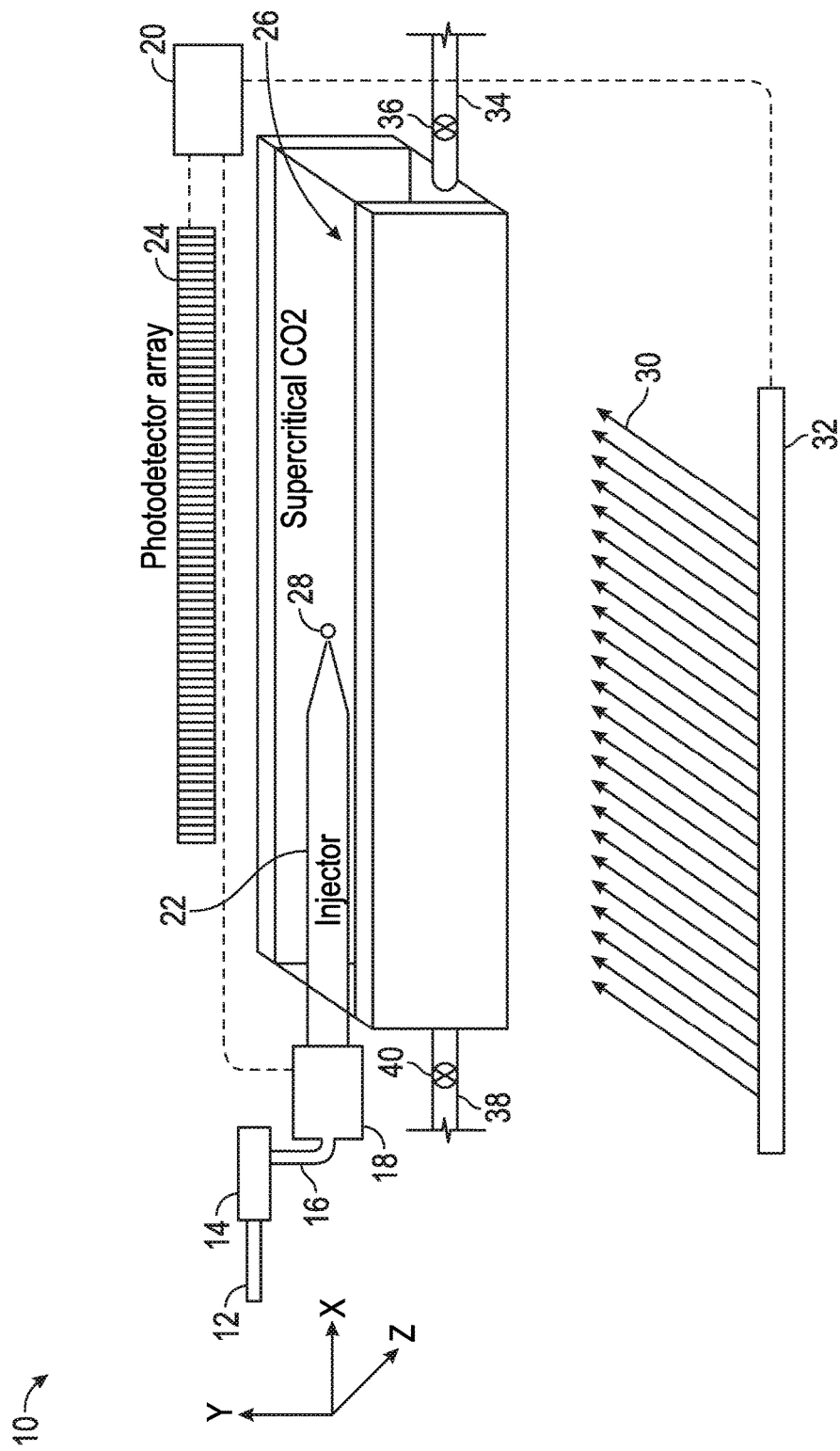
FIG. 1 illustrates a schematic view of a fluid analysis instrument in accordance with embodiments of the present disclosure.

Aspects of the present disclosure relate to fluid analysis. Chromatography is one known technique for analyzing fluids by separating the components. Traditional chromatography involves separating components (e.g., solutes) of a mixture on the basis of the relative amounts of each solute distributed between a moving fluid stream, called the flowing or mobile phase, and a "stationary" phase. The mobile phase may be either a liquid or a gas, while the stationary phase may be either a solid or a liquid. The mobile phase may be forced through the stationary phase. For example, High Performance Liquid Chromatography ('HPLC') and Gas Chromatography ('GC') use narrow tubes packed with a stationary phase, referred to as columns, through which the mobile phase is forced.

The phases are chosen such that components of the sample have differing solubilities in each phase. A component having the relatively greater solubility in the stationary phase will take longer to travel through it than a component having relatively lesser solubility in the stationary phase but remaining quite soluble in the mobile phase. As a result of these differences in mobilities, sample components will become separated from each other as they travel through the stationary phase.

Band broadening is a phenomenon that reduces the efficiency of the separation and leads to decreased performance. Band broadening is problematic in terms of both the quality of the separation obtained and the accuracy with which sample components can be quantified, with poor resolution being a particular result. The degree of band broadening tends to increase with the age of the column used. The Van Deemter equation describes some factors contributing to column band broadening, including longitudinal and eddy diffusion.

For traditional chromatography, diffusion can be quite problematic because it smears out the concentration band of a particular compound, which can cause its band to overlap in time with the immediately following and preceding compound bands.

The prior art of traditional chromatography requires several components, including, namely, a mixture sample desired to be separated into its individual components; a "stationary" phase, such as, for example, a silicone oil coating on the inside surface of a capillary tube in GC, or non-polar alkanes such as C-8 or C-18 chains on silica particles in LC; a flowing or "mobile" phase carrier fluid, such as, for example, Helium in gas chromatography (GC), that flows that mixture sample past the stationary phase; and the requirement that there be different affinities of the different components for the stationary phase compared to the mobile phase (i.e., different partition coefficients).

The stronger the affinity of a component for the stationary phase, the slower that component will move through the chromatograph. In this way, compounds in the mixture are separated from one another by their different exit times.

Aspects of the present disclosure include new chromatographic techniques based predominantly upon diffusion and iteratively modeling that diffusion. In aspects, the present disclosure leverages differences in diffusion between the components by measuring concentration of the components in a solvating fluid at various distances from an initial point over time. The present disclosure may rely upon diffusion of a mixture sample within a single fluid. Therefore, techniques of the present disclosure do not require a flowing phase that moves the mixture sample past a stationary phase for which different components within the mixture have different partition coefficients. Thus, the present disclosure has no requirement that the compounds to be distinguished have different partition coefficients but only that they have different diffusion coefficients.

In further aspects, this disclosure relates to taking a downhole measurement. Downhole measurement, as used herein, may be defined as a measurement taken in a borehole intersecting an earth formation indicative of a parameter of the borehole or the formation, i.e., a downhole parameter. Method embodiments may include taking measurements of a fluid sample, wherein the fluid is a downhole fluid. The fluid may be obtained downhole, and the measurements may be conducted downhole. In general embodiments, these measurements may be used in analysis and evaluation of the fluid and the formation.

The environment in subterranean wells presents a harsh environment. With increasing depth, the ambient temperature of the borehole environment becomes especially problematic. Most hydrocarbon wells will reach temperatures of at least 150 degrees Celsius. More challenging wells may reach temperatures of at least 175 degrees Celsius. High downhole temperatures may reach 200 degrees Celsius (392 degrees Fahrenheit) or more. Space in a downhole carrier (conveyance device) may be limited to a few inches in diameter.

Maintaining proper operation of tools in the downhole environment may be challenging, due to temperature and vibration. Instruments exposed to downhole fluids may suffer corrosive effects as well. Traditional chromatography would thus be very difficult to implement downhole. Additionally, cleaning of a traditional chromatograph between samples would also be difficult. There is also a risk of asphaltenes in the downhole fluid permanently plugging the chromatographic column.

Aspects of the present disclosure include novel diffusion-based chromatographic techniques applied within a borehole intersecting a subterranean formation to evaluate a downhole fluid. The downhole fluid may include a formation fluid. The downhole fluid may include one or more hydrocarbons.

General method embodiments include methods for evaluating a fluid using an instrument, including: introducing a sample comprising the fluid to a solvating fluid at a point in a chamber associated with the instrument at a first time to create a heterogeneous admixture; measuring concentrations of each of a plurality of components in the admixture at a plurality of distances from the point in the chamber at, at least one additional time later than the first time, each of the plurality of distances being non-zero; and estimating a relative concentration for each of the plurality of components in the fluid by extrapolating the relative concentration of each of the plurality of components in the sample at the point at the first time using the measured concentrations in the admixture at the plurality of distances. At least some of the measured concentrations of a particular component of the plurality of components at the plurality of distances are non-identical due to diffusion of the plurality of components over time.

Methods may include estimating a diffusion curve for each of the plurality of components from the measured concentrations; estimating a diffusion coefficient for each of the plurality of components from the diffusion curve; and estimating the relative concentration for each of the plurality of components using at least the diffusion coefficient.

Measuring the concentrations of each of the plurality of components at the plurality of distances may be carried out by providing illumination to the chamber; and using a plurality of optical sensors to detect, at each of the plurality of distances, absorption of wavelengths of the illumination that are characteristic of the plurality of components. The plurality of optical sensors may comprise at least one of: i) a photodiode array; and ii) a pyroelectric array. The illumination may comprise at least one of: i) visible light, ii) near-infrared light; and iii) mid-infrared light.

FIG. 1 illustrates a schematic view of a fluid analysis instrument in accordance with embodiments of the present disclosure. The instrument 10 includes an inlet port 12 providing the fluid to be analyzed to sample chamber 14. The sample chamber 14 is configured for receiving the fluid, and, in turn, is connected via an inlet conduit 16 to an injector 18. The injector 18 may include various valves, pumps, and other components as known in the art, and is operatively coupled to test chamber 26 via a stem 28. The distal end of stem 28 is configured to introduce fluid to a test chamber 26. Measurement components may include an illumination source 32 (e.g., light emitting diodes) configured to provide illumination 30 (near-infrared light) to the chamber 26; and an optical sensor array 24, comprising a plurality of optical sensors (e.g., photodiode array) configured to detect, at each of a plurality of distances, absorption of wavelengths of the illumination that are characteristic of the plurality of components. Illumination may be transmitted through a transparent chamber, or through transparent portions of the chamber ('windows'), or illumination source 32 may be located interior to the chamber. Similarly, sensor array 24 may be located interior to the chamber 26, or use transparent elements.

At least one processor 20, including suitable electronics and/or circuitry, is configured as a control unit to control the operation of the instrument, including injector 18, valves 36 and 40 controlling flow of the solvating fluid, and the measurement components. The at least one processor 20 may be configured to receive measurement data, store the data and/or transmit the data to a remote location.

The at least one processor 20 may control valve 40 to fill test chamber 26 with solvating fluid from solvating fluid inlet 38. When sufficient solvating fluid is accumulated in the chamber 26, the at least one processor 20 closes valve 40 to seal the chamber 26.

Processor 20 may cause operation of injector 18 and measurement components according to a common clock. The injector 18 is configured to inject a small sample of the fluid which is introduced to the test chamber. The injector 18 introduces the portion of the fluid, which may have a pressure higher than the ambient pressure ('high pressure') to the chamber 26 via stem 22 at a first time. For example, the fluid may be introduced at a pressure of at least one atmosphere higher than the ambient pressure. Intermittently, the illumination source 32 provides illumination 30 to the chamber 26, and the photodetector array 24 detects absorption of wavelengths of the illumination at each of a plurality of distances at additional later times. The at least one processor 20 measures concentrations of each of a plurality of components in the admixture at a plurality of distances from the point in the chamber at, at least one additional time later than the first time. The concentrations may be relative or absolute.

As one example, in operation, a small (e.g., approximately 1-5 microliters) sample may be injected at high pressure into the middle of a solvating fluid in the chamber, such as, for example, supercritical carbon dioxide ($CO_2$), or other supercritical fluid. The solvating fluid may be selected for its failure to absorb light at wavelengths absorbed by components of interest, which are suspected to be in the fluid and for which detection is desired. This is true for supercritical $CO_2$ and hydrocarbon-absorbing wavelengths.

It may be beneficial to introduce the fluid at a central point, or at least at some distance from the ends of the chamber, to avoid additional boundary restrictions. In the embodiment of FIG. 1, the boundaries constrain the available dilution volume (and thereby the diffusion opportunities) to substantially one dimension (+X or −X) along the axis of the injector with substantially no diffusion opportunities perpendicular to that direction (such as, +Y, −Y, +Z, −Z). In some implementations, however, such as, for example, wherein the instrument is incorporated as part of a downhole tool, it may be beneficial to introduce the fluid at an end of the chamber in order to fit within the tool dimensions, or to take advantage of specific boundary constraints.

Diffusion begins immediately upon introduction of the fluid. Lighter compounds diffuse faster. Therefore, at earlier times, only the lightest compound found in the fluid (e.g., methane, in the case of downhole fluids) is observed at long distances from the injection point. Concentrations at various distances from the injection point may be measured by the detected values of absorption (at a particular hydrocarbon wavelength) of infrared light along a many-pixel photodetector array.

The at least one processor may be configured for estimating a relative concentration for each of the plurality of components in the fluid by extrapolating the relative concentration of each of the plurality of components in the sample at the point at the first time using the measured concentrations in the admixture at the plurality of distances, as described above.

In some implementations estimating the relative concentrations may be carried out by, at the early times, fitting the diffusion equation curve to the concentration versus distance at long distances for the lightest compound, which allows calculation of its diffusion coefficient. See Feng et al. Molecular Dynamics Simulation of Diffusion and Structure of Some n-Alkanes in near Critical and Supercritical Carbon Dioxide at Infinite Dilution. *J. Phys. Chem. B* 2013, 117, 12525-12534.

Eventually, the lightest compound is joined by next lightest compound (e.g., ethane, in a downhole hydrocarbon context), and the combined concentration with respect to distance at distances along the length of the detector array is measured for this two-compound mixture, also by infrared absorption. The later measurements may be taken at times predetermined in accordance with theoretical or empirical diffusion data for the predicted compounds, or may be carried out in response to detected discontinuities in measurement data characteristic of the various stages of diffusion (e.g., sufficient diffusion by each compound in turn). Discontinuities in the slope of dA/dx with respect to x might be used to define the geometric boundaries of changes in the dominant component, wherein A is the concentration and x is the distance from the point of injection, for example. After subtracting the fitted diffusion curve of the lightest compound from the measurement curve of the two-compound measurements, the diffusion coefficient of the second lightest compound may be calculated. Next, the third lightest compound (e.g., propane) joins the first two compounds in the admixture at further distances from the initial point proximate the injector, and the whole process is repeated again.

By iteratively repeating the procedure, eventually diffusion coefficients and corresponding equations are obtained for each compound. Upon reaching this stage, the at least one processor may be configured to estimate a relative concentration for each of the plurality of components in the fluid by extrapolating the relative concentration of each of the plurality of components in the sample back to the injection point at the first time using the measured concentrations in the admixture at the plurality of distances. That is, the at least one processor may perform extrapolation back to zero time and zero distance to get the amounts of each compound at the injection point and time, thereby effectively creating a chromatogram.

When the operation is completed, valves 40 and 36 may be opened, and the chamber may be flushed with fresh $CO_2$ to remove the admixture. In some advantageous embodiments, the old, contaminated $CO_2$ may be run through a carbon filter or the like to remove the hydrocarbons, so that the $CO_2$ may be reused.

In alternative embodiments, mid-infrared light may be used for illumination and a pyroelectric array could be used for detection, which may result in stronger optical absorption. Also, instead of using absorption of light over a broad wavelength band associated with all hydrocarbons, narrow wavelength bands of light that distinguish between different hydrocarbons (methane, ethane, propane, etc.) could be used. See U. Liddel and C. Kasper, Spectral Differentiation of Pure Hydrocarbons: A Near Infrared Absorption Study. Research Paper RP610, *Part of Bureau of Standards Journal of Research*, Vol. 11, November 1933.

Estimating the relative concentration for each of the plurality of components in the fluid may be carried out using a model of the diffusion of each component. As one example, the sample may be modeled as a one-dimensional instantaneous point source, and its diffusion modeled in accordance with the transport equation describing the transport of scalar species in a fluid system. Known analytical solutions to the transport equation under different boundary and initial conditions may be employed.

Figure 2A:
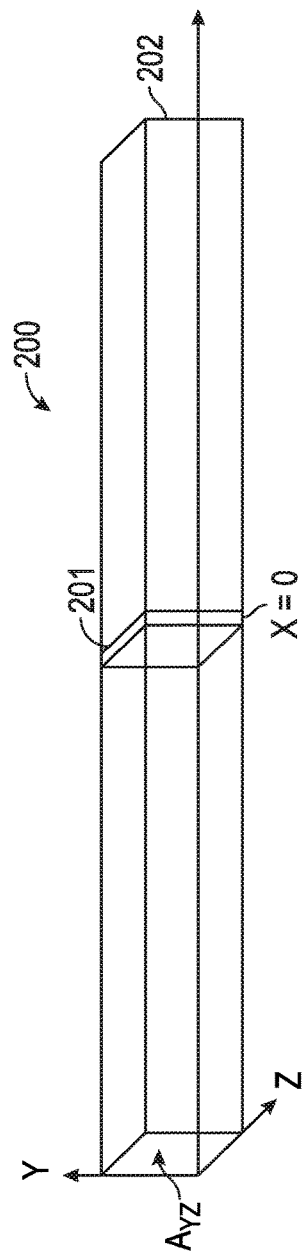
FIGS. 2a & 2b show models of diffusion in accordance with embodiments disclosed herein.
Figure 2B:
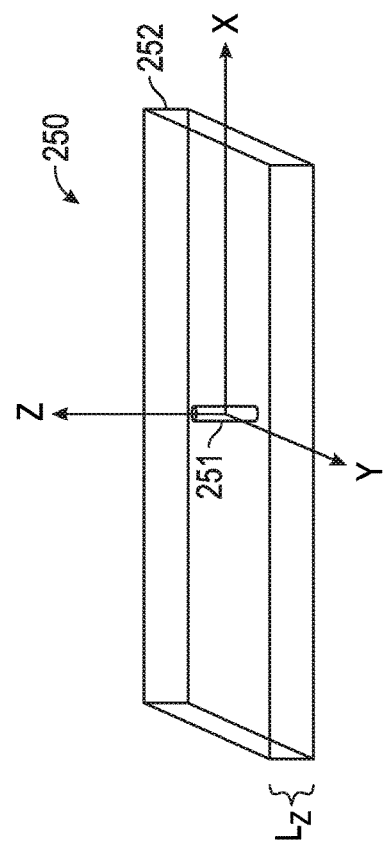

FIGS. 2a & 2b show diffusion of simulated components using models of diffusion in accordance with embodiments disclosed herein. FIG. 2a illustrates a model 200 showing an example solution describing the one-dimensional evolution of a slab of mass, M, that had been released instantaneously at time t=0 into a stationary fluid. Assuming a one-dimensional system in the x-direction, i.e. the system is uniform in y and z, such that $\partial/\partial y=0$ and $\partial/\partial z=0$, a slab of mass M 201 is released into the chamber 202, comprising a long, narrow tube. The mass is distributed uniformly in the y-z plane and with negligible dimension in x, such that the initial concentration is $C(x)=M\delta(x)$, where $\delta(\,)$ is the Dirac delta function.

With these initial conditions, and assuming that mass M of the sample is released at t=0 and x=0, the concentration distribution may be modeled as:

$$C(x, t) = \frac{M}{\sqrt{4\pi Dt}} \exp\left(-\frac{x^2}{4Dt}\right) = [M/L] \tag{1}$$

For conversion to a three-dimensional system, the concentration should have units of $M/L^3$. Conversion to real space may be accomplished by dividing by the neglected dimensions, e.g., the cross-sectional area of the system in the y-z plane, $A_{yz}$.

FIG. 2b illustrates a model 250 showing another example solution describing the two-dimensional evolution of a slug of mass, M, released instantaneously. The system is uniform in z, such that $\partial/\partial z = 0$. The mass slug 251 is distributed uniformly in z with negligible dimension in y and x, such that the initial concentration is $C(x, y, t=0) = M \delta(x) \delta(y)$, where $\delta( )$ is the Dirac delta function.

With these initial conditions for a two-dimensional system, and assuming that mass M of the sample is released at $t=0$ and $x=y=0$, the concentration distribution may be modeled as:

$$C(x, y, t) = \frac{M}{L_z 4\pi t \sqrt{D_x D_y}} \exp\left(-\frac{x^2}{4D_x t} - \frac{y^2}{4D_y t}\right) = [ML^{-3}]. \quad (2)$$

For conversion to a three-dimensional system, the concentration should have units of $M/L^3$. Thus, it should be noted the above results from recovering the correct concentration in real, three-dimensional space, by dividing the two-dimensional solution by the length of the missing dimension, e.g. $L_z$ in the figure given above.

Figure 3A:
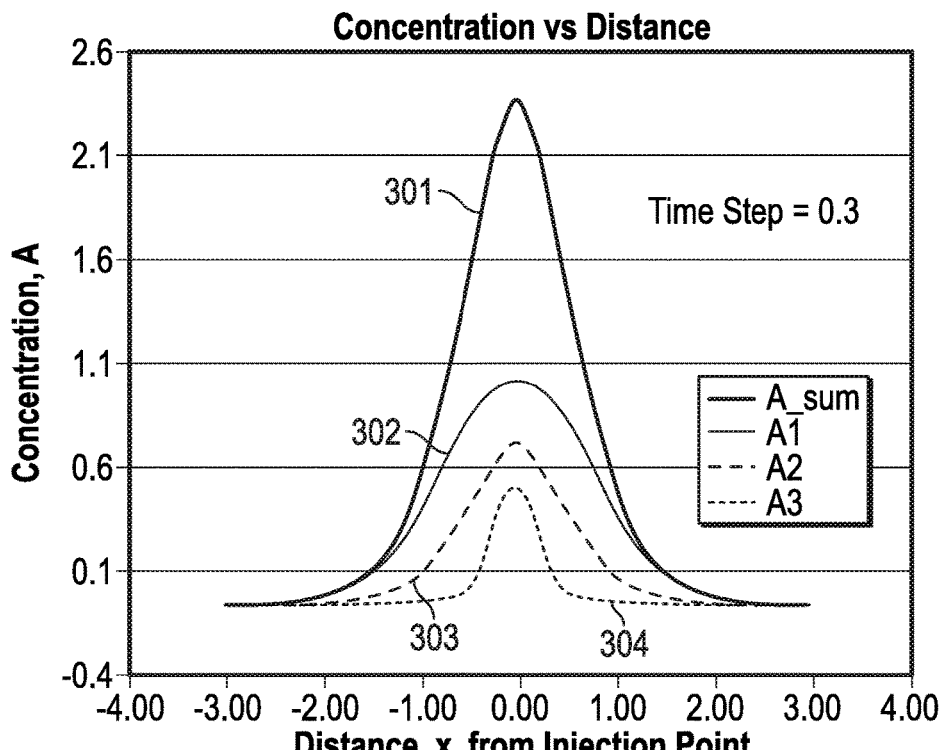
FIGS. 3a & 3b illustrate simulated one-dimensional diffusion curves at a first time (t=0.3) in accordance with embodiments of the present disclosure.
Figure 3B:
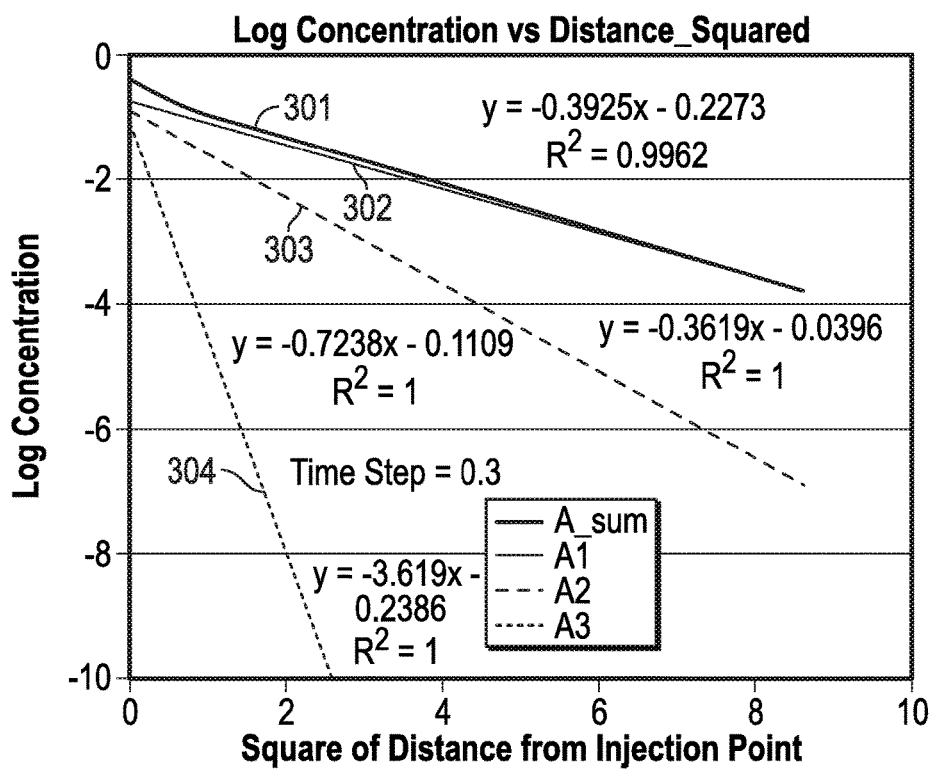

FIGS. 3a & 3b illustrate simulated one-dimensional diffusion curves at a first time (t=0.3) in accordance with embodiments of the present disclosure. FIG. 3a shows Gaussian one-dimensional simulated diffusion curves for three components, $A_1$ 302, $A_2$ 303, $A_3$ 304. FIG. 3b shows the same data re-plotted as $\log_{10}$ of concentration versus the square of distance from the injection point. Table 1 illustrates results for concentrations of the three components, $A_1$, $A_2$, $A_3$, at an early time (t=1.0) showing how, at that time, for several distances (−3.0, −2.9, and −2.8), the C1 concentration is at least 100 times greater than the C2 concentration, which is at least $10^{14}$ times greater than the C3 concentration, which is why the C2 and C3 concentrations can be ignored when fitting a diffusion equation to C1 for this time and these distances.

Gaussian one-dimensional simulated diffusion curves for three components, shows Gaussian one-dimensional simulated diffusion curves for three components, $A_1$ 402, $A_2$ 403, $A_3$ 404. FIG. 4b shows the same data re-plotted as $\log_{10}$ of concentration versus the square of distance from the injection point. $A_{sum}$ 401 is the sum of all concentrations, $A_1$, $A_2$, and $A_3$.

Figure 5A:
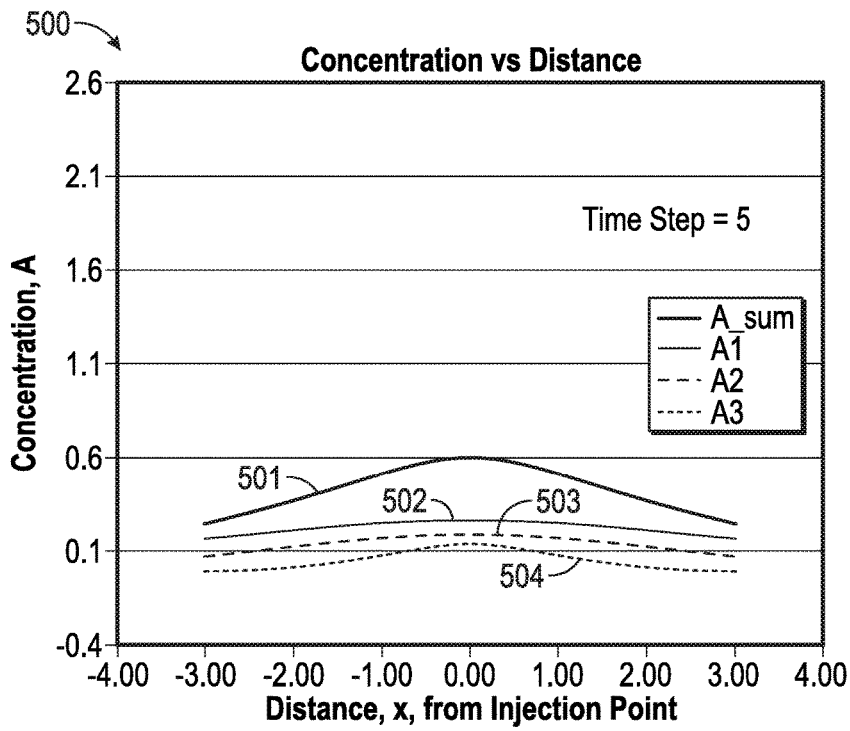
FIGS. 5a & 5b illustrate simulated diffusion curves at a second later time (t=5) in accordance with embodiments of the present disclosure.
Figure 5B:
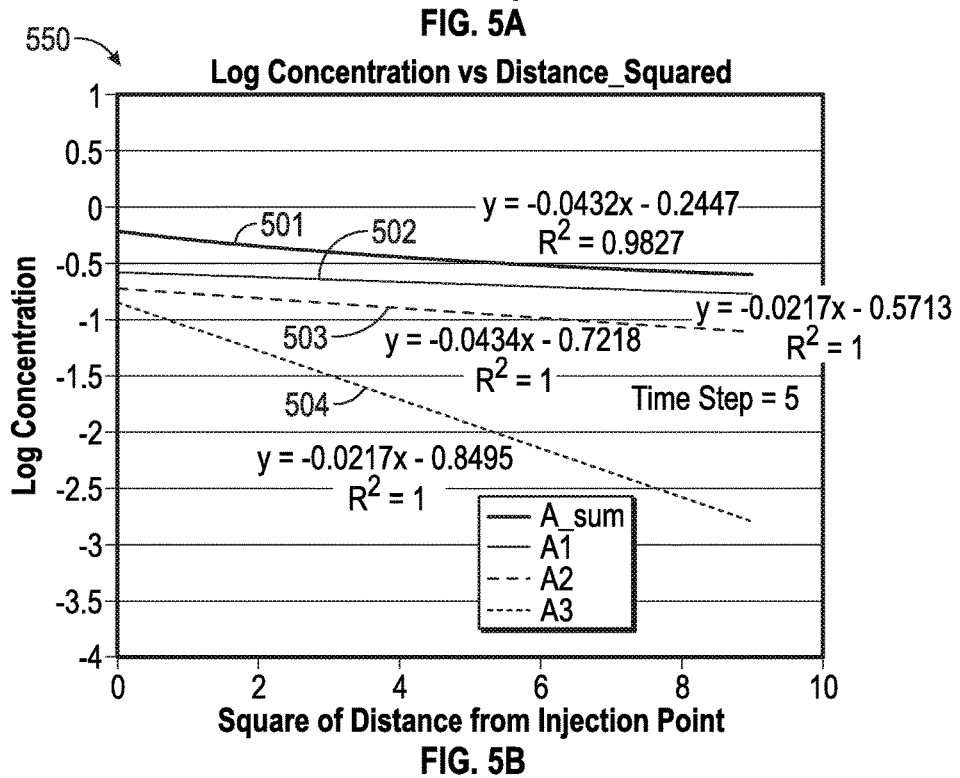

FIGS. 5a & 5b illustrate simulated diffusion curves at a second later time (t=5) in accordance with embodiments of the present disclosure. FIG. 5a shows Gaussian one-dimensional simulated diffusion curves for three components, $A_1$ 502, $A_2$ 503, $A_3$ 504. FIG. 5b shows the same data re-plotted as $\log_{10}$ of concentration versus the square of distance from the injection point. It is important to note that, as time progresses, all the measured data flattens out in concentration over distance. $A_{sum}$ 501 is the sum of all concentrations, $A_1$, $A_2$, and $A_3$.

Figure 6:
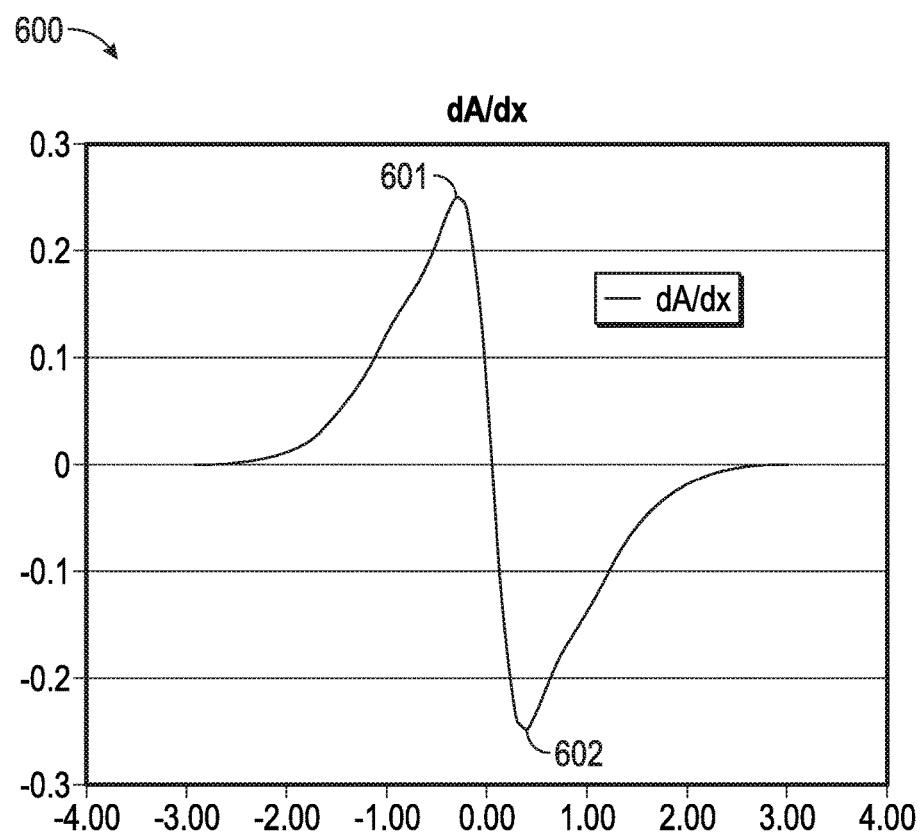
FIG. 6 shows simulated data with respect to changes in concentration.

FIG. 6 shows simulated data with respect to changes in concentration. Curve 600 plots $dA/dx$ with respect to x wherein A is the concentration and x is the distance from the point of injection. The changes in slope of curve 600, such as peak 601 and valley 602 may be used to define the geometric boundaries of changes in the dominant component, as described above.

As described above, where the absorption of the wavelengths is measured over a wavelength band sufficiently broad to be responsive to all of the plurality of components, the relative concentration of each of the plurality of components in the admixture may be estimated in sequence. However, in some embodiments, the absorption of the wavelengths may be measured using a plurality of wavelength bands, such that each of the plurality of components is characterized by one or more wavelength bands. That is, detectors specific to each wavelength expected to be absorbed—and corresponding to components anticipated to be in the admixture—may be employed in the array. In this way, the relative concentration of each of the plurality of components in the admixture may be estimated simultaneously, because they may be spectrally distinguished even when they overlap in time and space. See U. Liddel and C. Kasper.

| $x^2$ | t | x | $A_1$ | $A_2$ | $A_3$ | A_sum | dA/dx | $C_1/C_2$ | $C_2/C_3$ |
|---|---|---|---|---|---|---|---|---|---|
| 9 | 1 | −3.00 | 0.063240 | 0.004713 | 0.000000 | 0.067953 | | 180.0343 | 1.29E+16 |
| 8.41 | 1 | −2.90 | 0.073290 | 0.006330 | 0.000000 | 0.079621 | 0.011668 | 134.0412 | 1.22E+15 |
| 7.84 | 1 | −2.80 | 0.084515 | 0.008418 | 0.000000 | 0.092933 | 0.013312 | 100.8009 | 1.25E+14 |

In this simulation, at early times, $A_{sum}$ 301 (the sum of all concentrations, $A_1$, $A_2$, and $A_3$) is almost the same as $A_1$ at long distances, because $A_1$ has the highest diffusion coefficient. Thus, it gets out the farthest first. In this example, the mixture is 60 percent Compound 1, 30 percent Compound 2, and 10 percent Compound 3. Compound 1 has a diffusion constant 1, Compound 2 has a diffusion coefficient 0.5, and Compound 3 has a diffusion constant 0.1.

The slope of $\log_{10}$ of concentration versus distance squared equals $-1/(4 \cdot 2.303 \, D \, t)$, so knowing the time, t, the diffusion coefficient, D, can be calculated, where $2.303 = 1/\log_{10}(e)$.

Figure 4A:
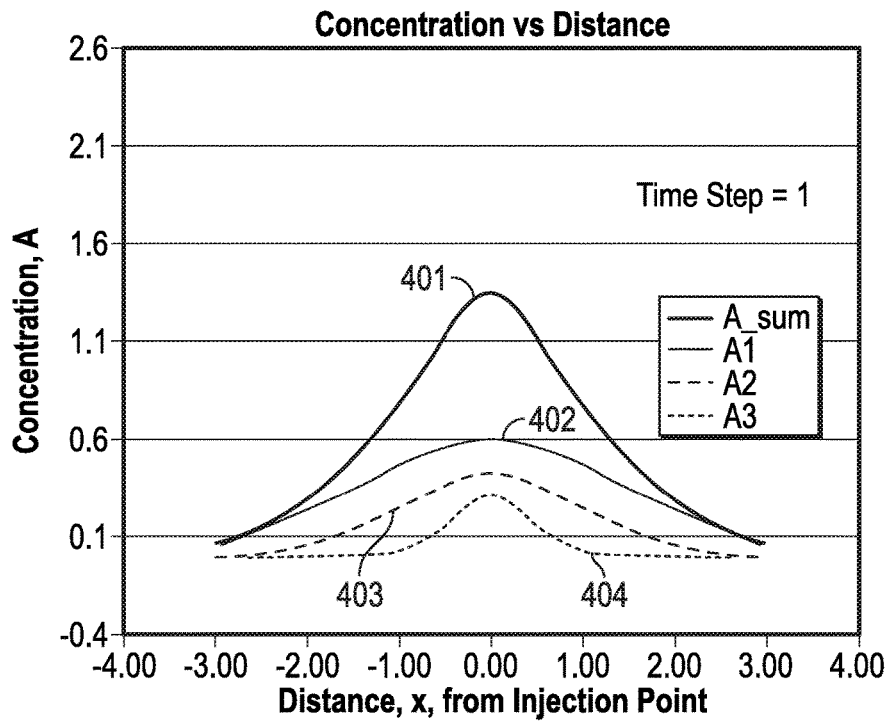
FIGS. 4a & 4b illustrate simulated one-dimensional diffusion curves at a first later time (t=1.0) in accordance with embodiments of the present disclosure.
Figure 4B:
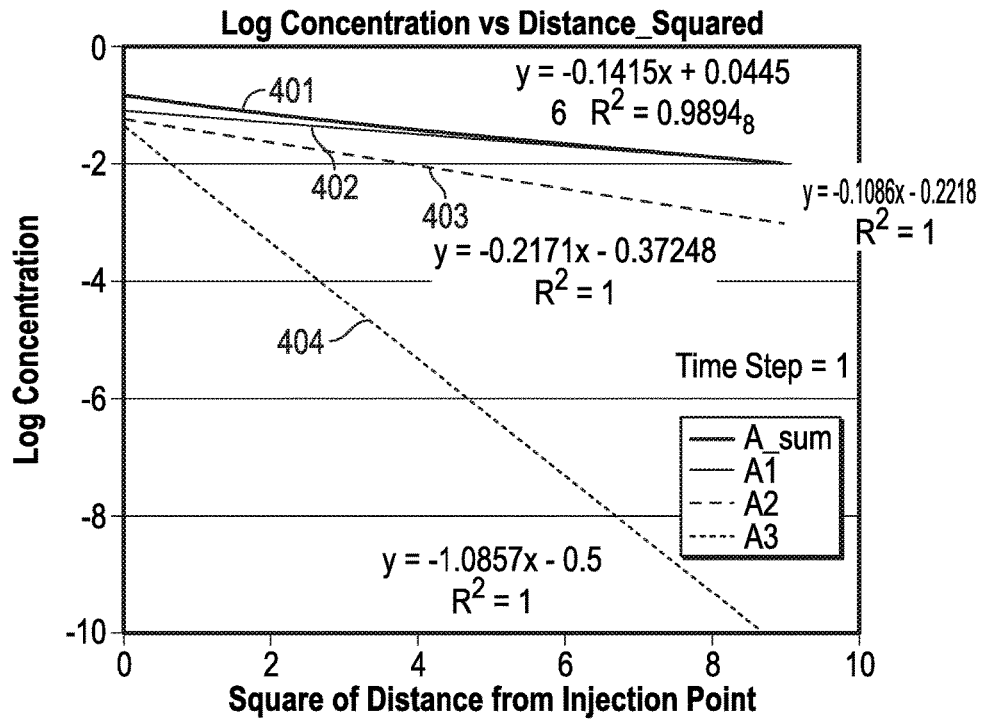

FIGS. 4a & 4b illustrate simulated one-dimensional diffusion curves at a first later time (t=1.0) in accordance with embodiments of the present disclosure. FIG. 4a shows Aspects of the present disclosure relate to apparatus and methods for downhole logging with respect to formation evaluation, including measurement and interpretation of physical phenomena indicative of parameters of interest of the formation, the borehole, or the downhole fluids therein. Techniques described herein are particularly suited to measurement of values of properties of a downhole fluid through the use of instruments utilizing diffusion phenomena. These values may be used to evaluate and model the fluid, the formation, or the borehole, and for conducting further operations in the formation or the borehole. Each of the embodiments herein may be used in a variety of settings in both drilling and non-drilling environments.

Aspects of the present disclosure relate to modeling a volume of an earth formation. The model of the earth formation generated and maintained in aspects of the disclosure may be implemented as a representation of the earth formation stored as information. The information (e.g., data) may be stored on a non-transitory machine-readable medium, transmitted, and rendered (e.g., visually depicted) on a display.

As used herein, the term "fluid" and "fluids" refers to one or more gasses, one or more liquids, and mixtures thereof. A "downhole fluid" as used herein includes any gas, liquid, flowable solid and other materials having a fluid property and relating to hydrocarbon recovery. A downhole fluid may be natural or man-made and may be transported downhole or may be recovered from a downhole location. Non-limiting examples of downhole fluids include drilling fluids, return fluids, formation fluids, production fluids containing one or more hydrocarbons, engineered fluids, oils and solvents used in conjunction with downhole tools, water, brine, and combinations thereof. An "engineered fluid" may be used herein to mean a human made fluid formulated for a particular purpose.

Figure 7:
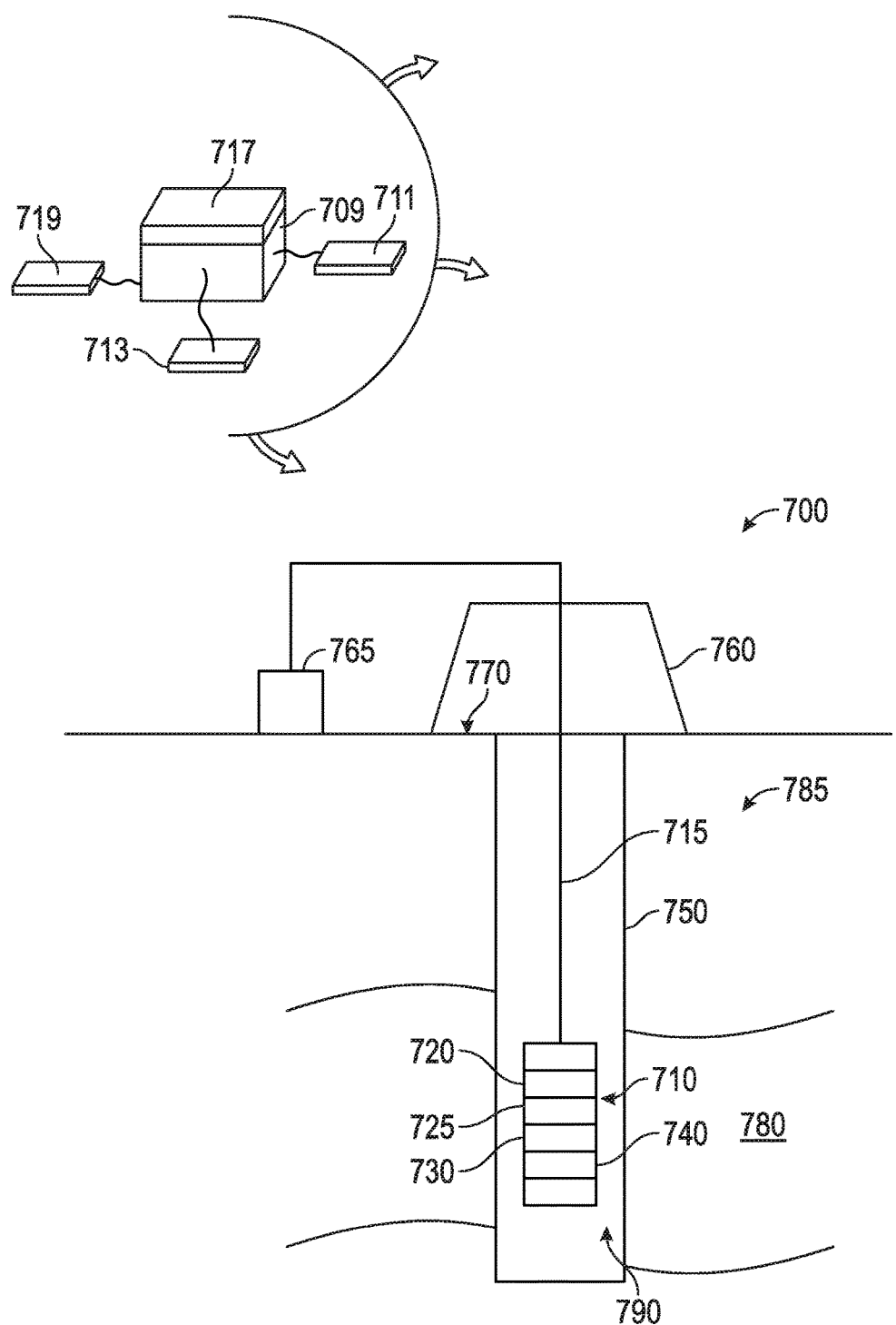
FIG. 7 schematically illustrates a system having a downhole tool configured to acquire information for estimating a downhole parameter of interest using a chromatography instrument in accordance with embodiments of the present disclosure.

FIG. 7 schematically illustrates a system 700 having a downhole tool 710 configured to acquire information for estimating a downhole parameter of interest (e.g., a value of a property of the formation 780, the borehole 750, or downhole fluid 790 therein) using chromatography instrument 740.

The system 700 may include a conventional derrick 760 erected on a derrick floor 770. A conveyance device (carrier 715) which may be rigid or non-rigid, may be configured to convey the downhole tool 710 into wellbore 750 in proximity to a volume of interest 780 of an earth formation 785. The carrier 715 may be a drill string, coiled tubing, a slickline, an e-line, a wireline, etc. Downhole tool 710 may be coupled or combined with additional tools e.g., some or all the information processing system (inset). Thus, depending on the configuration, the tool 710 may be used during drilling and/or after the wellbore 750 has been formed. As described herein, "borehole" or "wellbore" refers to a single hole that makes up all or part of a drilled well. While a land system is shown, the teachings of the present disclosure may also be utilized in offshore or subsea applications. The carrier 715 may include embedded conductors for power and/or data for providing signal and/or power communication between the surface and downhole equipment (e.g., a seven conductor cable). The carrier 715 may include a bottom hole assembly, which may include a drilling motor for rotating a drill bit.

Downhole fluid (e.g., drilling fluid, or 'mud') 790 may be present between the formation 785 and the downhole tool 710. A surface control system 765 receives signals from instrument(s) 740 or electronics 730 indicative of measurements of the downhole fluid 790 and other sensors used in the system 700 and processes such signals according to programmed instructions provided to the surface control system 765. The surface control system 765 may display desired parameters and other information on a display/monitor that is utilized by an operator. The surface control system 765 may further communicate with a downhole control system 720 at a suitable location on downhole tool 710. The surface control system 765 may process data relating to the operations and data from the instrument 740, and may control one or more downhole operations performed by system 700, including operation of fluid collection system 725.

In one embodiment, electronics 730 associated with instrument 740 may be configured to record and/or process the information obtained. Certain embodiments of the present disclosure may be implemented with a hardware environment that includes an information processor 717, an information storage medium 713, an input device 711, processor memory 709, and may include peripheral information storage medium 719. The hardware environment may be in the well, at the rig, or at a remote location. Moreover, the several components of the hardware environment may be distributed among those locations. The input device 711 may be any data reader or user input device, such as data card reader, keyboard, USB port, etc. The information storage medium 713 stores information provided by the detectors. Information storage medium 713 may include any non-transitory computer-readable medium for standard computer information storage, such as a USB drive, memory stick, hard disk, removable RAM, EPROMs, EAROMs, flash memories and optical disks or other commonly used memory storage system known to one of ordinary skill in the art including Internet based storage. Information storage medium 713 stores a program that when executed causes information processor 717 to execute the disclosed method. Information storage medium 713 may also store the formation information provided by the user, or the formation information may be stored in a peripheral information storage medium 719, which may be any standard computer information storage device, such as a USB drive, memory stick, hard disk, removable RAM, or other commonly used memory storage system known to one of ordinary skill in the art including Internet based storage. Information processor 717 may be any form of computer or mathematical processing hardware, including Internet based hardware. When the program is loaded from information storage medium 713 into processor memory 709 (e.g. computer RAM), the program, when executed, causes information processor 717 to retrieve detector information from either information storage medium 713 or peripheral information storage medium 719 and process the information to estimate a parameter of interest. Information processor 717 may be located on the surface or downhole.

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, an information processing device includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

To perform the treatments during a single trip, the tool may use a high bandwidth transmission to transmit the information acquired by electronics 730 via instrument 740 to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control operations in "substantially real-time."

One point of novelty of the system illustrated in FIG. 7 is that the surface control system 765 and/or the downhole control system 720 are configured to perform certain methods (discussed below) that are not in the prior art. A surface control system or downhole control system may be configured to control the tool described above and any incorporated sensors and to estimate a parameter of interest according to methods described herein.

Aspects of the present disclosure are subject to application in various different embodiments. In some general embodiments, carrier 715 is implemented as a tool string of a drilling system, and measurements taken in the borehole may be characterized as "logging-while-drilling" (LWD) or "measurement-while-drilling" (MWD) operations.

Figure 8:
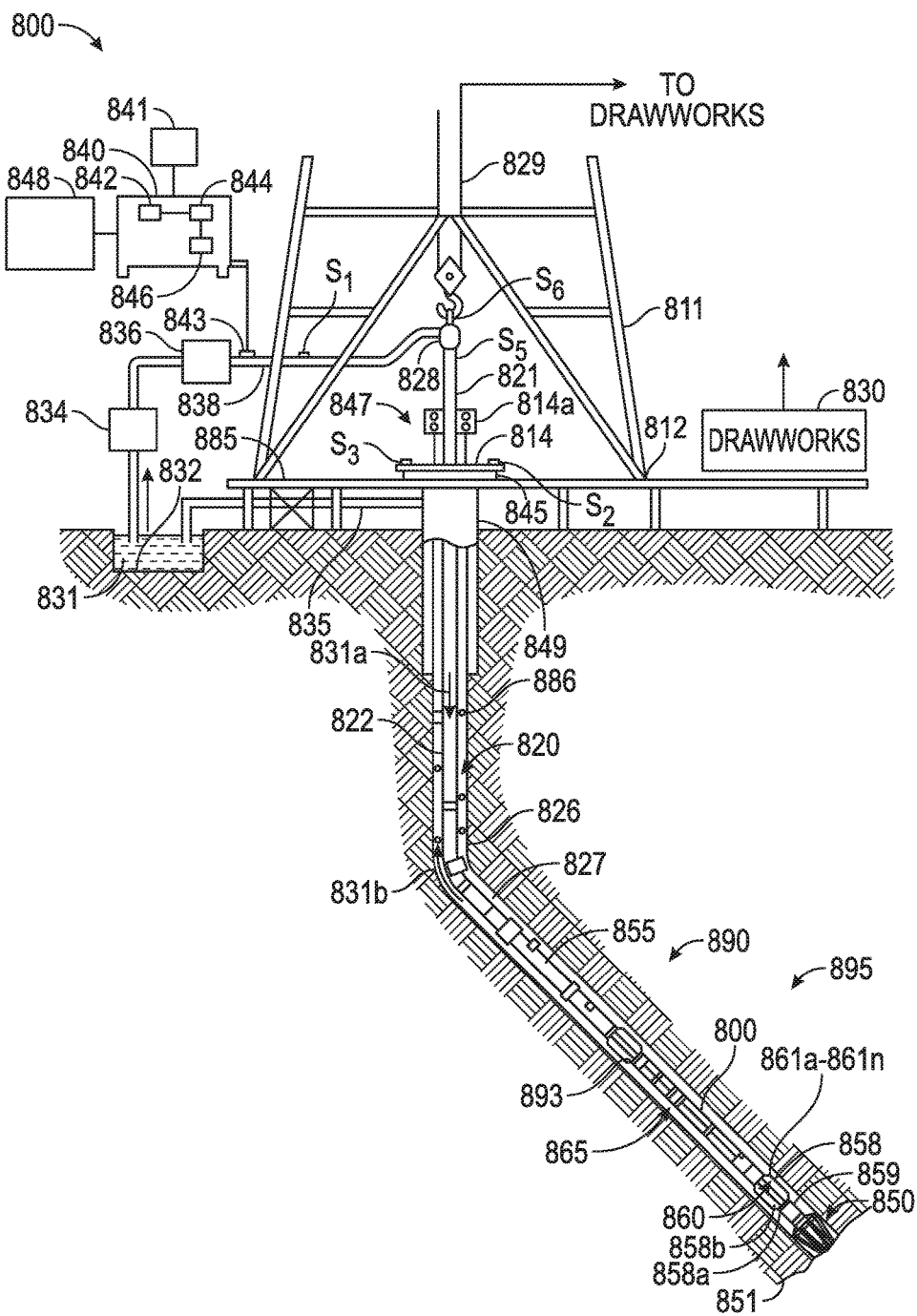
FIG. 8 shows an example embodiment of an MWD system for downhole evaluation using diffusion-based chromatography.

FIG. 8 shows an example embodiment of an MWD system for downhole evaluation using diffusion-based chromatography. The system 801 includes a carrier 811 that is shown disposed in a wellbore or borehole 826 that penetrates at least one earth formation 895. The system 801 also includes a tool 810 configured for conducting diffusion-based fluid analysis in the borehole.

FIG. 8 shows a drill string 820 including a bottomhole assembly (BHA) 890 conveyed in the borehole 826 as the carrier. The drilling system 801 includes a conventional derrick 811 erected on a platform or floor 812 which supports a rotary table 814 that is rotated by a prime mover, such as an electric motor (not shown), at a desired rotational speed. A tubing (such as jointed drill pipe 822), having the drilling assembly 890, attached at its bottom end extends from the surface to the bottom 851 of the borehole 826. A drill bit 850, attached to drilling assembly 890, disintegrates the geological formations when it is rotated to drill the borehole 826. The drill string 820 is coupled to a drawworks 830 via a Kelly joint 821, swivel 828 and line 829 through a pulley. Drawworks 830 is operated to control the weight on bit ("WOB"). The drill string 820 may be rotated by a top drive (not shown) instead of by the prime mover and the rotary table 814. Alternatively, a coiled-tubing may be used as the tubing 822. A tubing injector 814*a* may be used to convey the coiled-tubing having the drilling assembly attached to its bottom end. The operations of the drawworks 830 and the tubing injector 814*a* are known in the art and are thus not described in detail herein.

It should be understood that embodiments of the present disclosure are well suited for use in wells having various configurations including horizontal wells, deviated wells, slanted wells, multilateral wells and so on. Accordingly, use of directional terms herein (e.g., above, below, upper, lower, upward, downward, topmost, lowermost, uphole, downhole, etc) refer to the direction of travel along the borehole either toward or away from the surface, with the upward direction being toward the surface and the downward direction being away from the surface.

A suitable drilling fluid 831 (also referred to as the "mud") from a source 832 thereof, such as a mud pit, is circulated under pressure through the drill string 820 by a mud pump 834. The drilling fluid 831 passes from the mud pump 834 into the drill string 820 via a discharger 836 and the fluid line 838. The drilling fluid 831*a* from the drilling tubular discharges at the borehole bottom 851 through openings in the drill bit 850. The returning drilling fluid 831*b* circulates uphole through the annular space 827 between the drill string 820 and the borehole 826 and returns to the mud pit 832 via a return line 835 and drill cutting screen 885 that removes the drill cuttings 886 from the returning drilling fluid 831*b*. A sensor S1 in line 838 provides information about the fluid flow rate. A surface torque sensor S2 and a sensor S3 associated with the drill string 820 respectively provide information about the torque and the rotational speed of the drill string 820. Tubing injection speed is determined from the sensor S5, while the sensor S6 provides the hook load of the drill string 820.

Well control system 847 is placed at the top end of the borehole 826. The well control system 847 includes a surface blow-out-preventer (BOP) stack 815 and a surface choke 849 in communication with a wellbore annulus 827. The surface choke 849 can control the flow of fluid out of the borehole 826 to provide a back pressure as needed to control the well.

In some applications, the drill bit 850 is rotated by only rotating the drill pipe 822. However, in many other applications, a downhole motor 855 (mud motor) disposed in the BHA 890 also rotates the drill bit 850. The rate of penetration (ROP) for a given BHA largely depends on the WOB or the thrust force on the drill bit 850 and its rotational speed.

A surface control unit or controller 840 receives signals from the downhole sensors and devices via a sensor 843 placed in the fluid line 838 and signals from sensors S1-S6 and other sensors used in the system 801 and processes such signals according to programmed instructions provided to the surface control unit 840. The surface control unit 840 displays drilling parameters and other parameters of interest related to the borehole, formation, and drilling operations, and other information on a display/monitor 841 that is utilized by an operator to control the drilling operations. The surface control unit 840 may be a computer-based unit that may include a processor 842 (such as a microprocessor), a storage device 844, such as a solid-state memory, tape or hard disc, and one or more computer programs 846 in the storage device 844 that are accessible to the processor 842 for executing instructions contained in such programs. The surface control unit 840 may further communicate with a remote control unit 848. The surface control unit 840 may process data relating to the drilling operations, data from the sensors and devices on the surface, and data received from downhole; and may control one or more operations of the downhole and surface devices. The data may be transmitted in analog or digital form.

The BHA 890 may include a tool 810 configured for performing diffusion-based fluid analysis downhole. The BHA 890 may also contain other formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the formation 895 surrounding the BHA 850. For convenience, all such sensors are generally denoted herein by numeral 865. The BHA 890 may further include a variety of other sensors and devices 859 for determining one or more properties of the BHA 890, such as vibration, bending moment, acceleration, oscillations, whirl, stick-slip, weight-on-bit, fluid flow rate, pressure, temperature, rate of penetration, azimuth, tool face, drill bit rotation, etc.

The BHA 890 may include a steering apparatus or tool 858 for steering the drill bit 850 along a desired drilling path. In one aspect, the steering apparatus may include a steering unit 860, having a number of force application members 861*a*-861*n*. The force application members may be mounted directly on the drill string, or they may be at least partially integrated into the drilling motor. In another aspect, the force application members may be mounted on a sleeve, which is rotatable about the center axis of the drill string. The force application members may be activated using electro-mechanical, electro-hydraulic or mud-hydraulic actuators. In yet another embodiment the steering apparatus may include a steering unit 858 having a bent sub and a first steering device 858a to orient the bent sub in the wellbore and the second steering device 858b to maintain the bent sub along a selected drilling direction. The steering unit 858, 860 may include near-bit inclinometers and magnetometers.

The drilling system 801 may include sensors, circuitry and processing software and algorithms for providing information about desired drilling parameters relating to the BHA, drill string, the drill bit and downhole equipment such as a drilling motor, steering unit, thrusters, etc. Many current drilling systems, especially for drilling highly deviated and horizontal wellbores, utilize coiled-tubing for conveying the drilling assembly downhole. In such applications a thruster may be deployed in the drill string 820 to provide the required force on the drill bit.

Example sensors for determining drilling parameters include, but are not limited to drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling, and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by BAKER HUGHES INCORPORATED.

The drilling system 801 can include one or more downhole processors at a suitable location such as 893 on the BHA 890. The processor(s) can be a microprocessor that uses a computer program implemented on a suitable non-transitory computer-readable medium that enables the processor to perform the control of system 801 and processing of information, such as information from the sensors. The non-transitory computer-readable medium may include one or more ROMs, EPROMs, EAROMs, EEPROMs, flash memories, RAMs, hard drives and/or optical disks. Other equipment such as power and data buses, power supplies, and the like will be apparent to one skilled in the art. In one embodiment, the MWD system utilizes mud pulse telemetry to communicate data from a downhole location to the surface while drilling operations take place. The surface processor 842 can process at the surface measured data, along with the data transmitted from the downhole processor, to evaluate the formation.

Surface processor 842 or downhole processor 893 may also be configured to control steering apparatus 858, mud pump 834, drawworks 830, rotary table 814, downhole motor 855, other components of the BHA 890, or other components of the drilling system 801. Surface processor 842 or downhole processor 893 may be configured to control diffusion-based analysis instruments as described above and to estimate a parameter of interest according to methods described herein.

Control of these components may be carried out using one or more models using methods described below. For example, surface processor 842 or downhole processor 893 may be configured to modify drilling operations i) autonomously upon triggering conditions, ii) in response to operator commands, or iii) combinations of these. Such modifications may include changing drilling parameters, steering the drillbit (e.g., geosteering), altering the drilling fluid program, activating well control measures, and so on. Control of these devices, and of the various processes of the drilling system generally, may be carried out in a completely automated fashion or through interaction with personnel via notifications, graphical representations, user interfaces and the like. Reference information accessible to the processor may also be used. In some general embodiments, surface processor 842, downhole processor 893, or other processors (e.g. remote processors) may be configured to operate the diffusion-based fluid analysis tool.

The system 801 may include any number of downhole tools for various processes including formation drilling, geosteering, and formation evaluation (FE) for making electrical measurements versus depth and/or time of one or more physical properties in or around a borehole, including a volume of interest of the formation intersected by the borehole.

Mathematical models, look-up tables, or other models representing relationships between the signals and the parameter values may be used to characterize the borehole, downhole fluid, operations in the formation or the formation itself, optimize one or more operational parameters of a production or development, and so on. The system may carry out these actions through notifications, advice, and/or intelligent control. Various types of downhole parameters may be determined using measurements in accordance with the present disclosure and making evaluations in accordance with embodiments disclosed herein.

Figure 9:
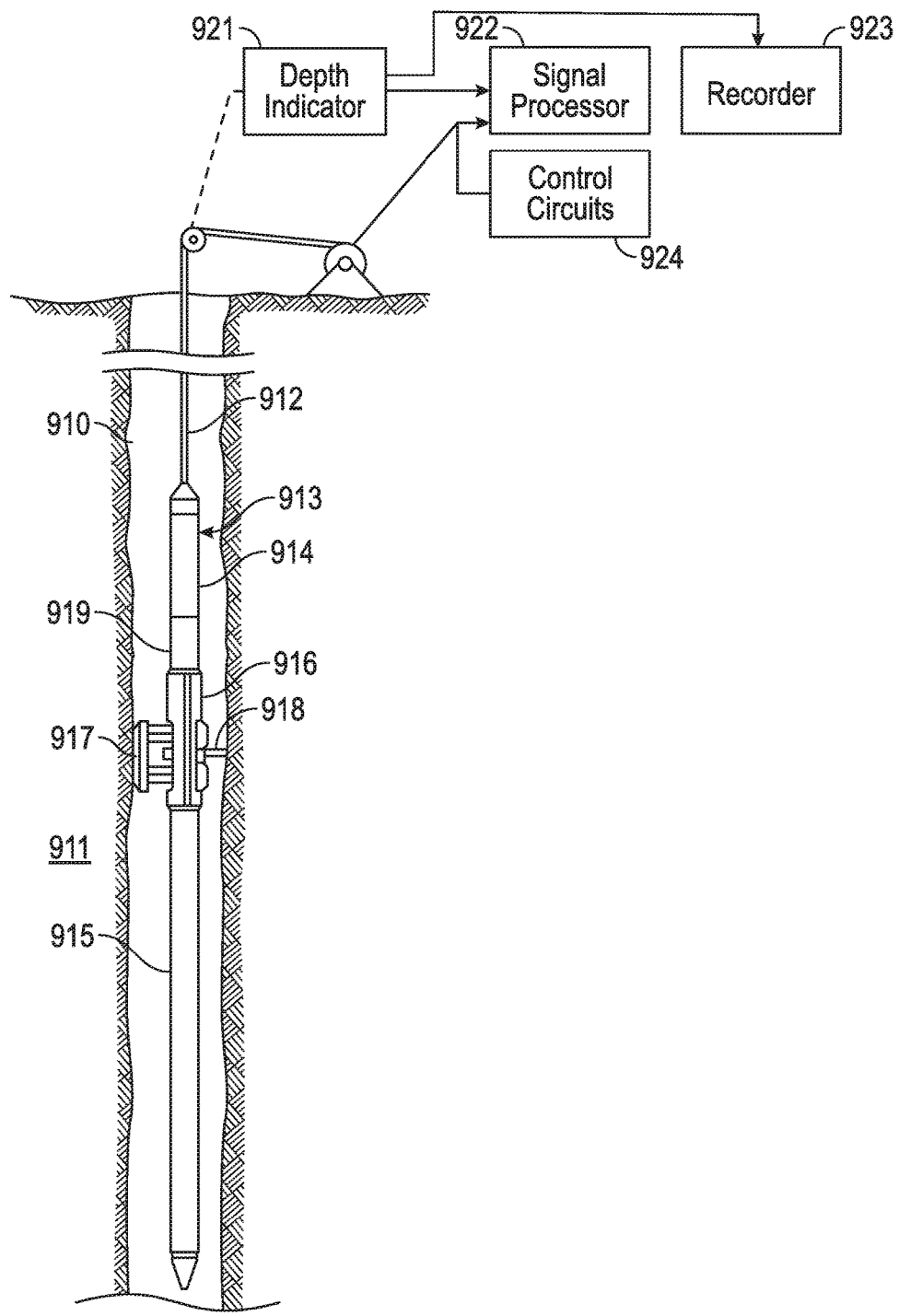
FIG. 9 illustrates a wireline tool in accordance with embodiments of the present disclosure in communication with the formation.

FIG. 9 illustrates a wireline tool in accordance with embodiments of the present disclosure in communication with the formation. Borehole 910 intersects a portion of the earth formation 911. Disposed within the borehole 910 by means of a carrier 912 is a sampling and measuring tool 913 including a diffusion-based chromatography instrument as described above. Carrier 912 may be a drill string, coiled tubing, a slickline, an e-line, a wireline, etc. The sampling and measuring instrument includes hydraulic power system 919, a fluid sample storage section 915 and a sampling mechanism section 916. Sampling mechanism section 916 includes selectively extensible well engaging pad member 917, a selectively extensible fluid admitting sampling probe member 918 and bi-directional pumping member 919. Specific configuration of the components with respect to one another may vary.

In operation, sampling and measuring instrument 913 is positioned within borehole 910 via carrier 912 (e.g., by winding or unwinding cable 912 from a hoist (not shown)). Depth information from a depth indicator 921 is coupled to signal processor 922 and recorder 923 when tool 913 is disposed adjacent an earth formation of interest. Control signals from control circuitry 929 are transmitted through electrical conductors contained within conveyance device 912 to tool 913. Any or all of signal processor 922, control circuitry 929 and recorder 923 may be implemented with one more processors.

Electrical control signals activate an operational hydraulic pump within the hydraulic power system 919 shown, which provides hydraulic power causing the well engaging pad member 917 and the fluid admitting member 918 to move laterally from tool 913 into engagement with the earth formation 911 and the bi-directional pumping member 919. Fluid admitting member or sampling probe 918 can then be placed in fluid communication with the earth formation 911, such as, for example, via electrical control signals from control circuits 929 selectively activating solenoid valves within tool 913 for the taking of a sample of connate fluids contained in the earth formation of interest, or via other actuation techniques. Other collection systems may be used in other embodiments, such as, for example, a system for continuously sampling borehole fluid.

Figure 10:
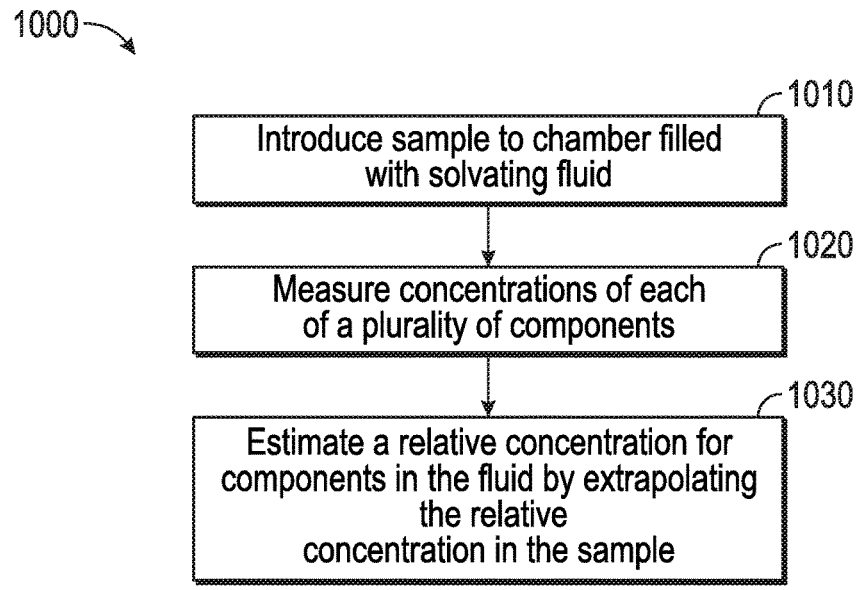
FIG. 10 illustrates methods for evaluating a fluid using an instrument in accordance with embodiments of the present disclosure.

FIG. 10 shows a flow chart 1000 for evaluating a fluid using an instrument in accordance with embodiments of the present disclosure. Step 1010 comprises introducing a sample comprising the fluid to a solvating fluid at a point in a chamber associated with the instrument at a first time to create a heterogeneous admixture. This may be carried out by injecting the sample. The sample may be injected in the solvating fluid in the chamber at a pressure greater than an ambient pressure of the solvating fluid. The solvating fluid may be supercritical carbon dioxide.

Step 1020 comprises measuring concentrations of each of a plurality of components in the admixture at a plurality of distances from the point in the chamber at, at least one additional time later than the first time. Each of the plurality of distances are non-zero. Measuring the concentrations of each of the plurality of components at the plurality of distances may include providing illumination to the chamber; and using a plurality of optical sensors to detect, at each of the plurality of distances, absorption of wavelengths of the illumination that are characteristic of the plurality of components. At least some of the measured concentrations of a particular component of the plurality of components at the plurality of distances are non-identical due to diffusion of the plurality of components over time.

Step 1030 comprises estimating a relative concentration for each of the plurality of components in the fluid by extrapolating the relative concentration of each of the plurality of components in the sample at the point at the first time using the measured concentrations in the admixture at the plurality of distances. Estimating the relative concentrations may involve applying a model. The model may include, but is not limited to, (i) a mathematical equation, (ii) an algorithm, (iii) a database of associated parameters, or a combination thereof. Step 1030 may be carried out by estimating a diffusion curve for each of the plurality of components from the measured concentrations; estimating a diffusion coefficient for each of the plurality of components from the diffusion curve; and estimating the relative concentration for each of the plurality of components using at least the diffusion coefficient.

The absorption of the wavelengths may be measured over a wavelength band sufficiently broad to be responsive to all of the plurality of components. The relative concentration of each of the plurality of components in the admixture may be estimated in sequence. The sequence includes a plurality of stages. The first stage begins at a first additional time of the at least one additional time after introducing the sample.

The first stage may include: i) measuring concentrations of a lightest component of the plurality of components at the plurality of distances from the point; ii) estimating the diffusion curve for the lightest component from the concentrations of the lightest component; iii) estimating the diffusion coefficient for the lightest component from the corresponding diffusion curve for the lightest component; and iv) performing additional measurement cycles.

The sequence may include additional stages iteratively performed on a lightest component untested in a preceding stage. Each additional stage may be carried out by: i) allowing the lightest component untested of the plurality of components to reach sufficient diffusion by waiting for another time interval; ii) measuring concentrations of the lightest component untested in combination with tested components at the plurality of distances; iii) estimating the diffusion curve for the lightest component untested from the measured concentrations of the lightest component untested in combination with tested components at the plurality of distances using the diffusion curve corresponding to each of the tested components; and iv) estimating the diffusion coefficient for the lightest component untested from the diffusion curve for the lightest component untested.

Estimating the diffusion curve for the lightest component untested from the measured concentrations of the lightest component untested in combination with the tested components at the plurality of distances may include estimating a cumulative diffusion curve for the lightest component untested in combination with tested components; and subtracting the diffusion curves corresponding to each of the tested components from the cumulative diffusion curve to estimate the diffusion curve for the lightest component untested.

Optional steps may include estimating a parameter of interest of the fluid using the estimated relative concentration for each of the plurality of components or other information. The parameter of interest may be applied to a model. Further optional steps may include transmitting and/or displaying a representation of the model, the parameter of interest, or the concentrations.

Other optional steps may include conducting further operations in the earth formation in dependence upon the estimation. Further operations may include at least one of: i) extending the borehole; ii) drilling additional boreholes in the formation; iii) performing seismic measurements on the formation; iv) performing borehole logging in the formation; v) installing casing in the borehole; vi) evaluating casing installed in the borehole; and vii) producing one or more hydrocarbons from the formation. This may be carried out by conducting further operations in dependence upon the model in which the estimation has been incorporated.

Figure 11:
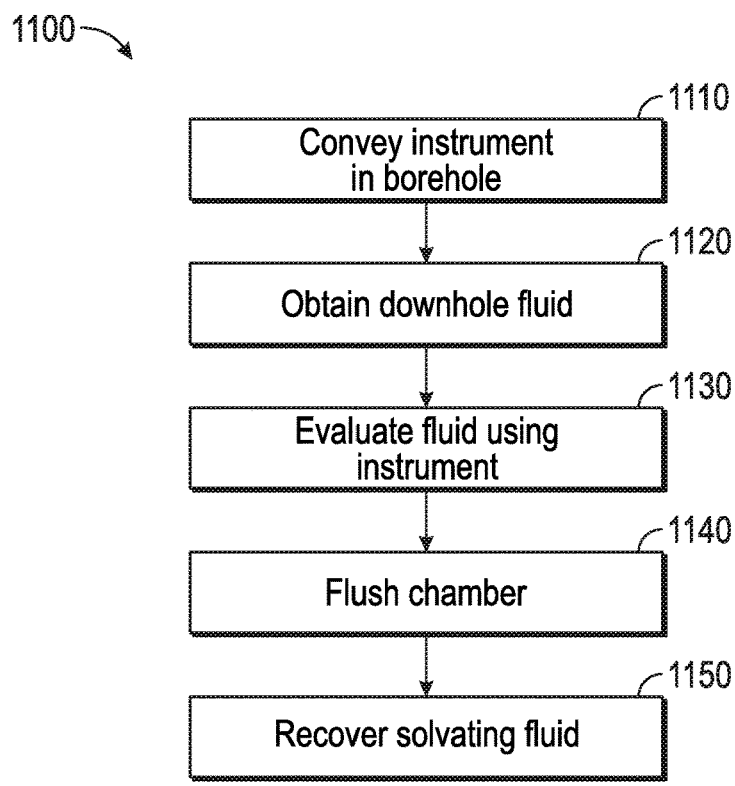
FIG. 11 shows a flow chart illustrating methods for evaluating a downhole fluid in a borehole intersecting the earth formation using an instrument in accordance with embodiments of the present disclosure.

FIG. 11 shows a flow chart 1100 for evaluating a downhole fluid in a borehole intersecting the earth formation using an instrument in accordance with embodiments of the present disclosure. In step 1110, the method comprises conveying the instrument in the borehole. Step 1110 may be carried out by conveying a sampling tool in the borehole, wherein the instrument is associated with the sampling tool. Step 1120 may include obtaining the downhole fluid. In some implementations, obtaining the downhole fluid comprises drawing the downhole fluid into the tool. Step 1130 may include evaluating the fluid using the instrument, as described above with respect to FIG. 10, to estimate the relative concentration of one or more components. After measurement is complete, Step 1140 comprises flushing the chamber of the solvating fluid admixture. Optional step 1150 may include filtering the admixture to recover the solvating fluid. Other optional steps include repeating the measurement cycle and reusing the solvating fluid on additional samples.

Herein, "information" may include raw data, processed data, analog signals, and digital signals. Estimation of the parameter may include the use of a model. In some embodiments, the model may include, but is not limited to, one or more of: (i) a mathematical equation, (ii) an algorithm, (iii) an deconvolution technique, and so on. The at least one parameter of interest may include, but is not limited to, one or more of: (i) viscosity, (ii) chemical composition, (iii) permittivity, (iv) density.

In some aspects, this disclosure relates to estimating a parameter of interest related to a volume of an earth formation, such as, for example, an earth formation surrounding a borehole. The parameter of interest may be a physical characteristic of the volume, such as, for example, density.

The term "carrier" as used above means any device, device component, combination of devices, media and/or member that may be used to convey, house, support or otherwise facilitate the use of another device, device component, combination of devices, media and/or member. Example non-limiting conveyance devices include drill strings of the coiled tube type, of the jointed pipe type and any combination or portion thereof. Other conveyance device examples include casing pipes, wirelines, wire line sondes, slickline sondes, drop shots, downhole subs, BHA's, drill string inserts, modules, internal housings and substrate portions thereof, self-propelled tractors. The term "processor" herein includes, but is not limited to, any device that transmits, receives, manipulates, converts, calculates, modulates, transposes, carries, stores or otherwise utilizes information. A processor refers to any circuitry performing the above, and may include a microprocessor, resident memory, and/or peripherals for executing programmed instructions, application specific integrated circuits (ASICs), field programmable gate arrays (FPGAs), or any other circuitry configured to execute logic to perform methods as described herein. The term "information" as used above includes any form of information (Analog, digital, EM, printed, etc.). An information processing device may include a microprocessor, resident memory, and peripherals for executing programmed instructions.

In several non-limiting aspects of the disclosure, a processor includes a computer that executes programmed instructions for performing various methods. These instructions may provide for equipment operation, control, data collection and analysis and other functions in addition to the functions described in this disclosure, and may be stored on a non-transitory machine-readable medium accessible to the processor. Thus, configuration of the processor may include operative connection with resident memory and peripherals for executing programmed instructions. The processor may execute instructions stored in computer memory accessible to the processor, or may alternatively employ logic implemented as field-programmable gate arrays ('FPGAs'), application-specific integrated circuits ('ASICs'), other combinatorial or sequential logic hardware, and so on. The non-transitory machine-readable medium may include ROMs, EPROMs, EAROMs, Flash Memories, Optical disks, and Hard disks. As noted above, the processing may be done downhole or at the surface, by using one or more processors. In addition, results of the processing, such as an image of a resistivity property or permittivity, can be stored on a suitable medium.

The term "substantially real-time" as applied to methods of the present disclosure refers to an action performed (e.g., estimation, modeling, and so on) while the sensor is still downhole, after the generation of the information and prior to movement of the sensor of a distance of 100 meters, 50 meters, 25 meters, 10 meters, or less; and may be defined as estimation of the parameter of interest or production of the current iteration of a model within 15 minutes of generating the information, within 10 minutes of generation, within 5 minutes of generation, within 3 minutes of generation, within 2 minutes of generation, within 1 minute of generation, or less.

While the foregoing disclosure is directed to the one mode embodiments of the disclosure, various modifications will be apparent to those skilled in the art. It is intended that all variations be embraced by the foregoing disclosure.

What is claimed is:

1. A method of evaluating a fluid using an instrument, the method comprising:
   introducing a sample comprising the fluid to a solvating fluid at a point in a chamber associated with the instrument at a first time to create a heterogeneous admixture;
   measuring concentrations of each of a plurality of components in the admixture at a plurality of distances from the point in the chamber at at least one additional time later than the first time by:
   i) providing illumination to the chamber; and
   ii) using a plurality of optical sensors to detect, at each of the plurality of distances, absorption of wavelengths of the illumination that are characteristic of the plurality of components;
   using at least one processor to iteratively model diffusion of the fluid including estimating a relative concentration for each of the plurality of components in the fluid by extrapolating the relative concentration of each of the plurality of components in the sample at the point at the first time using the measured concentrations in the admixture at the plurality of distances, comprising:
   estimating a diffusion curve for each of the plurality of components from the measured concentrations; and
   estimating a diffusion coefficient for each of the plurality of components from the diffusion curve; and
   estimating the relative concentration for each of the plurality of components using at least the diffusion coefficient;
   wherein each of the plurality of distances is non-zero, the solvating fluid is configured to fail to absorb light at wavelengths absorbed by the plurality of components, and at least some of the measured concentrations of a particular component of the plurality of components at the plurality of distances are non-identical due to diffusion of the plurality of components over time.

2. The method of claim 1, wherein the solvating fluid is supercritical carbon dioxide, and the sample is injected in the solvating fluid in the chamber at a pressure greater than an ambient pressure of the solvating fluid.

3. The method of claim 1, wherein the plurality of optical sensors comprise at least one of: i) a photodiode array; and ii) a pyroelectric array.

4. The method of claim 1, wherein the illumination comprises at least one of: i) near-infrared light; and ii) mid-infrared light.

5. The method of claim 1, wherein the absorption of the wavelengths is measured using a plurality of wavelength bands such that each of the plurality of components is characterized by one or more wavelength bands, and wherein the relative concentration of each of the plurality of components in the admixture is estimated simultaneously.

6. The method of claim 1, wherein the absorption of the wavelengths is measured over a wavelength band sufficiently broad to be responsive to all of the plurality of components, and the relative concentration of each of the plurality of components in the admixture is estimated in sequence.

7. The method of claim 6, wherein the sequence includes a plurality of stages and wherein the first stage begins at a first additional time of the at least one additional time after introducing the sample, the first stage comprising:
   i) measuring concentrations of a lightest component of the plurality of components at the plurality of distances from the point;
   ii) estimating the diffusion curve for the lightest component from the concentrations of the lightest component;

iii) estimating the diffusion coefficient for the lightest component from the corresponding diffusion curve for the lightest component; and iv) performing additional measurement cycles.

8. The method of claim 7, wherein the sequence comprises additional stages iteratively performed on a lightest component untested in a preceding stage, each additional stage comprising:
i) allowing the lightest component untested of the plurality of components to reach sufficient diffusion by waiting for another time interval;
ii) measuring concentrations of the lightest component untested in combination with tested components at the plurality of distances;
iii) estimating the diffusion curve for the lightest component untested from the measured concentrations of the lightest component untested in combination with tested components at the plurality of distances using the diffusion curve corresponding to each of the tested components;
iv) estimating the diffusion coefficient for the lightest component untested from the diffusion curve for the lightest component untested.

9. The method of claim 8, wherein estimating the diffusion curve for the lightest component untested from the measured concentrations of the lightest component untested in combination with the tested components at the plurality of distances comprises:
estimating a cumulative diffusion curve for the lightest component untested in combination with tested components; and
subtracting the diffusion curves corresponding to each of the tested components from the cumulative diffusion curve to estimate the diffusion curve for the lightest component untested.

10. The method of claim 1, wherein the components comprise hydrocarbons.

11. The method of claim 1, comprising filtering the admixture to recover the solvating fluid; and reusing the solvating fluid on additional samples.

12. The method of claim 1, comprising estimating a parameter of interest of the fluid using at least a portion of the estimated relative concentration for each of the plurality of components.

13. The method of claim 1, wherein the fluid comprises a downhole fluid obtained using a borehole intersecting an earth formation.

14. The method of claim 13 further comprising:
conveying a sampling tool in the borehole, wherein the instrument is associated with the sampling tool;
drawing the downhole fluid into the tool.

15. An apparatus for evaluating a fluid using an instrument, the apparatus comprising:
a chamber associated with the instrument fillable with solvating fluid;
a source of solvating fluid coupled to the chamber;
an injector configured to introduce the fluid to the chamber;
an illumination source;
an optical sensor array; and
at least one processor configured to:
fill the chamber with solvating fluid from the source of solvating fluid;
introduce a sample comprising the fluid to the solvating fluid at a point in the chamber at a first time using the injector to create a heterogeneous admixture;
measure concentrations of each of a plurality of components in the admixture at a plurality of distances from the point in the chamber at at least one additional time later than the first time by:
i) providing illumination to the chamber; and
ii) using a plurality of optical sensors to detect, at each of the plurality of distances, absorption of wavelengths of the illumination that are characteristic of the plurality of components;
use at least one processor to iteratively model diffusion of the fluid including estimating a relative concentration for each of the plurality of components in the fluid by extrapolating the relative concentration of each of the plurality of components in the sample at the point at the first time using the measured concentrations in the admixture at the plurality of distances, comprising:
estimating a diffusion curve for each of the plurality of components from the measured concentrations; and
estimating a diffusion coefficient for each of the plurality of components from the diffusion curve; and
estimating the relative concentration for each of the plurality of components using at least the diffusion coefficient;
wherein each of the plurality of distances is non-zero, the solvating fluid is configured to fail to absorb light at wavelengths absorbed by the plurality of components, and at least some of the measured concentrations of a particular component of the plurality of components at the plurality of distances are non-identical due to diffusion of the plurality of components over time.

* * * * *